(12) United States Patent
Hatada et al.

(10) Patent No.: US 6,638,748 B2
(45) Date of Patent: Oct. 28, 2003

(54) GENE ENCODING ALKALINE LIQUIFYING ALPHA-AMYLASE

(75) Inventors: Yuji Hatada, Tochigi (JP); Katsuya Ozaki, Tochigi (JP); Katsutoshi Ara, Tochigi (JP); Shuji Kawai, Tochigi (JP); Susumu Ito, Tochigi (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/986,676

(22) Filed: Nov. 9, 2001

(65) Prior Publication Data

US 2002/0102698 A1 Aug. 1, 2002

Related U.S. Application Data

(62) Division of application No. 08/952,741, filed as application No. PCT/JP96/01641 on Jun. 14, 1996.

(30) Foreign Application Priority Data

Jun. 14, 1995 (JP) .............................. 7-147257

(51) Int. Cl.⁷ .......................... C12N 9/28; C12N 1/21; C12N 15/52; C07H 21/04
(52) U.S. Cl. ............... 435/202; 435/252.3; 435/252.33; 435/320.1; 536/23.2
(58) Field of Search .............................. 435/202, 252.3, 435/252.33, 320.1; 536/23.2

(56) References Cited

FOREIGN PATENT DOCUMENTS

| EP | 0410498 A3 | 1/1991 |
| EP | 0670367 A1 | 9/1995 |
| WO | WO 9426881 A1 | 11/1994 |
| WO | WO 9526397 A1 | 10/1995 |

OTHER PUBLICATIONS

Tsukamoto et al., "Nucleotide Sequence of the Maltohexaose–Producing Amylase Gene From An Alkalophilic *Bacillus sp.* #707 and Structural Similarity to Liquefying Typeα–Amylases," *Biochemical and Biophysical Research Communications*, vo. 151, No. 1, pp. 25–31 (1988).

Yukki et al., "Complete Nucleotide Sequence of a Gene Coding for Heat– and pH–Stable α–Amylase of *Bacillus licheniformis*: Comparison of the Amino Acid Sequences of Three Bacterial Liquefying α–Amylases Deduced from the DNA Sequences," *Journal of Biochemistry*, vol. 98, No. 5, pp. 1147–1156 (1985).

*Primary Examiner*—Elizabeth Slobodyansky
(74) *Attorney, Agent, or Firm*—Birch, Stewart, Kolasch & Birch, LLP

(57) ABSTRACT

The present invention is directed to a liquefying alkaline alpha-amylase, and a DNA encoding for the same and functional fragments thereof.

6 Claims, 4 Drawing Sheets

FIG. 3

```
primer 1    5' TAGACGCAGTAAAACACATAAA  3'
               C T C C   G T C
               G   G G       T
               T   T T primer 2    3' CGACAATGAAAACAACTATTAGTACT 5'
               G G G G G G G
               C C C   C
               T T T   T primer 3    5' AGCCAATCTCTCGTATAGCTGTA  3' primer 4    5' GTACAAAAACACCCTATACATG  3' primer 5    5' AATGGAACAATGATGCAGTA  3'
                  T T        T primer 6    5' CATTTGGCAAATGCCATTCAAA  3' primer 7    5' AAAATTGATCCACTTCTGCAG  3' primer A    5' CAGCGCGTGATAATATAAATTTGAAT  3' primer B    5' AAGCTTCCAATTTATATTGGGTGTAT  3'
```

GENE ENCODING ALKALINE LIQUIFYING ALPHA-AMYLASE

This application is a divisional of co-pending application Ser. No. 08/952,741, filed on Nov. 25, 1997 and for which priority is claimed under 35 U.S.C. 120. Application Ser. No. 08/952,741 is the national phase of PCT International Application No. PCT/JP96/01641 filed on Jun. 14, 1996 under 35 U.S.C. §371. The entire contents of each of the above-identified applications are hereby incorporated by reference. This application also claims priority of Application No. 147257/1995 filed in Japan on Jun. 14, 1995 under 35 U.S.C. §119.

TECHNICAL FIELD

The present invention relates to the gene encoding alkaline liquifying α-amylase and fragments thereof, and to recombinant DNA and a transformant bearing the gene or fragments of the gene.

BACKGROUND ART

Alpha-amylase has long been used in a variety of fields. For example, it has been used for the saccharification of grains and potatoes in the fermentation industry, as starch paste removers in the textile industry, as digestives in the pharmaceutical industry, and for the manufacture of thick malt syrups in the food industry. Alpha-amylase is an enzyme which acts on a starch-related polysaccharides such as amylose and amylopectin, hydrolyzing solely the α-1,4-glucoside bond of the polysaccharide molecule. Since 1833, when Payen and Persoz first discovered the enzyme, crystalline samples or electrophoretically homogeneous samples of α-amylase have been obtained from a number of different sources including bacteria, fungi, plant seeds, and animal digestive glands.

The present inventors have recently discovered that the efficacy of dish-washing detergents and laundry detergents for clothes can be greatly improved, particularly on starch dirts, when α-amylase and a debranching enzyme are both incorporated into these detergents (Japanese Patent Application Laid-open (kokai) No. 2-132192). However, most of the α-amylases previously found in the natural world exhibit maximal and stable enzymatic activities in the neutral to acidic pH ranges, but scarcely work in an alkaline solution of pH 9–10. There exist only a small number of amylase enzymes that are known to exhibit maximal activities in the alkaline pH range (so-called alkaline α-amylases and alkali-resistant α-amylases). These alkaline α-amylases and alkali-resistant α-amylase include, an enzyme produced by Bacillus sp. A-40-2 [Horikoshi, K. et al., *Agric. Biol. Chem.*, 35, 1783 (1971)], an enzyme produced by Bacillus sp. NRRL B-3881 [Boyer, E., *J. Baciteriol.*, 110, 992 (1972)], an enzyme produced by Streptomyces sp. KSM-9 (Japanese Patent Application Laid-Open (kokai) No. 61-209528, an enzyme produced by Bacillus sp. H-167 (Japanese Patent Application Laid-Open (kokai) No. 62-208278, an enzyme produced by *Bacillus alkalothermophilus* A3-8 (Japanese Patent Application Laid-Open (kokai) No. 2-49584, and an enzyme produced by Natronococcus sp. Ah-36 (Japanese Patent Application Laid-Open (kokai) No. 4-211369.

As used herein, the term "alkaline α-amylase" refers to α-amylases whose optimum pHs fall within the alkaline pH range, whereas the term "alkali-resistant α-amylase" refers to α-amylases which have optimum pHs within the neutral to acidic range but whose activities in the alkaline range are comparable with those obtained at an optimum pH, and in addition, which retain their stabilities in the alkaline range. By the term "neutral range" is meant the range of pH not less than 6 and less than 8, and the term "alkaline" denotes a pH which is higher than the "neutral range".

Most of these alkaline α-amylases and alkali-resistant amylases are so-called saccharifying α-amylases which decompose starch or starch-related polysaccharides to glucose, maltose, or maltotriose. As such, these enzymes cause problems if they are used as enzymes for detergents, though they are advantageously used in the manufacture of sugar. Thus, there remains a need for so-called alkaline liquefying α-amylases which exhibit resistance against surfactants used in detergents, and which decompose starch or starch-related polysaccharides in a highly random manner. The present inventors continued an extensive search for microorganisms producing an alkaline liquefying α-amylase suitable as a detergent component, and they discovered that an alkalophilic Bacillus sp. KSM-AP1378 strain, having its optimum pH for growth in the alkaline range, produces an enzyme exhibiting the activity of an alkaline liquefying α-amylase. They elucidated that this enzyme is useful as an additive in detergent compositions for washing dishes and kitchen utensils and for detergent compositions for clothes (WO94/26881).

Amounts of the enzyme produced may be effectively increased by improving a method for culturing an alkaline liquefying α-amylase-producing microorganism, Bacillus sp. KSM-AP1378, or by exploiting mutation. However, in order to produce the enzyme advantageously on an industrial scale, another approach must be taken.

Amounts of an enzyme produced can be enhanced using a genetic engineering approach, and in addition, the catalytic properties of the enzyme can be improved, using a protein engineering approach, by altering the gene encoding the enzyme. However, the gene encoding an alkaline liquefying α-amylase has not yet been obtained.

Accordingly, an object of the present invention is to provide the gene encoding alkaline liquefying α-amylase and fragments thereof, a transformant harboring recombinant DNA comprising the gene, and a method for producing an alkaline liquefying α-amylase using the transformant.

The DNA encoding the alkaline liquefying α-amylase gene may be further used to produce probes to be used in the isolation of additional, homologous alkaline liquefying α-amylase genes from other microorganisms. Thus, an additional object of the present invention is to provide a means of screening for and isolating additional alkaline liquefying α-amylase enzymes.

DISCLOSURE OF THE INVENTION

The present inventors attempted to isolate, from the chromosomal DNA of an alkalophilic Bacillus strain, a DNA fragment containing the gene encoding an alkaline liquefying α-amylase, and as a result, they were successful in isolating an approximately 1.8 kb DNA fragment encoding an alkaline liquefying α-amylase. When they transformed a host microorganism using this DNA fragment ligated to a suitable vector, it was confirmed that the resultant recombinant microorganism produced an alkaline liquefying α-amylase. Moreover, it was found that the amino acid sequence of the alkaline liquefying α-amylase to be encoded is different from that of previously known amylases. The present invention was accomplished based on this finding.

Accordingly, the present invention provides a DNA fragment encoding an alkaline liquefying α-amylase.

The present invention also provides a recombinant DNA comprising the above-described DNA fragment encoding an alkaline liquefying α-amylase.

The present invention also provides a transformed microorganism harboring the above-described recombinant DNA comprising a DNA fragment encoding an alkaline liquefying α-amylase.

The present invention further provides a method for producing an alkaline liquefying α-amylase, by culturing the above-described transformed microorganism and collecting the enzyme.

BRIEF DESCRIPTION OF THE DRAWINGS

FIG. 3 shows nucleotide sequences of primers 1–7 and primers A–B used (SEQ ID NOS: 3–9, and 10–11, respectively).

BEST MODE FOR CARRYING OUT THE INVENTION

Figure 1:
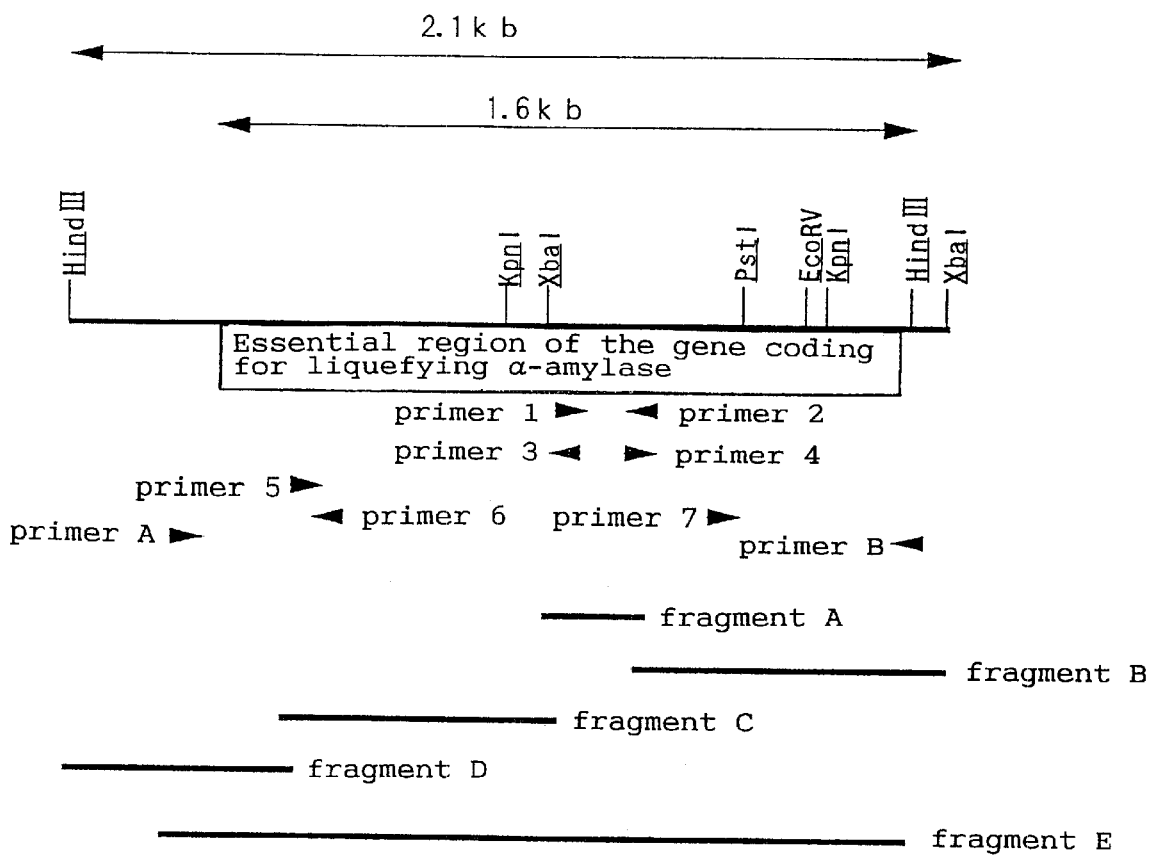
FIG. 1 shows a restriction enzyme map of a fragment of the gene encoding an alkaline liquefying amylase.

In the present invention, a useful microorganism which serves as an alkaline liquefying α-amylase gene donor may be, for example, Bacillus sp. KSM-AP1378 (FERM BP-3048, deposited Jul. 24, 1989 in Fermentation Research Institute, Agency of Industrial Science and Technology of 1-3, Higashi 1-chome, Tsukuba-shi, Ibaraki, 305 Japan), which is an alkalophilic Bacillus strain. This strain was isolated from the soil in the vicinity of the city of Tochigi in Tochigi Prefecture, Japan by the present inventors and identified as a strain which produces significant amounts of alkaline liquefying α-amylase. This strain was deposited at the Fermentation Research Institute, Agency of Industrial Science and Technology (1-3, Higashi 1-chome, Tsukuba-shi, Ibaraki-ken, 305, Japan) under FERM BP-3048 on Aug. 8, 1990 (originally deposited as P-10886 on Jul. 24, 1989).

In order to obtain chromosomal DNA from a donor microorganism, the method proposed by Marmur, J. (*J. Mol. Biol.,* 3, 208 (1961)) or the method proposed by Saito, H. and Miura, K. (*Biochem. Biophys. Acta,* 72, 619 (1963)) may be used. Other similar methods may also be used.

DNA fragments comprising the alkaline liquefying α-amylase gene are prepared by cleaving the thus-obtained chromosomal DNA using restriction enzymes. Restriction enzymes which may be used are not particularly limited so long as they do not fragment the gene. The alkaline liquefying α-amylase gene may also be obtained by PCR (Mullis, K. B. and Faloona, F. A., *Methods Enzymol.,* 155, 335 (1987); Saiki, R. K. et al., *Science,* 239, 487 (1988). For example, the gene may be obtained through the synthesis of primers having sequences corresponding to those on the upstream side of the 5'-terminus and on the downstream side of the 3'-terminus of the essential region based on the nucleotide sequence described in SEQ ID NO:1, and subsequently conducting PCR using, the chromosomal DNA of an alkaline liquefying α-amylase-producing microorganism as a template. Alternatively, an intact gene may be obtained by first obtaining a fragment of the alkaline liquefying α-amylase gene from an alkaline liquefying α-amylase-producing microorganism using any procedure, followed by PCR which amplifies the upstream and downstream sides of the fragmentary gene.

The thus-prepared genetic fragment is then subjected to cloning. Host/vector systems which may be used are not particularly limited, so far as that host bacterial strains express the alkaline liquefying α-amylase gene of the present invention, that the recombinant DNA molecules can be replicated in the host bacteria, and that the integrated gene can be stably harbored. For example, members of the EK system in which the host is *E. coli* K-12, and members of the BS system in which the host is *Bacillus subtilis* Marburg, may be used. Use of the EK system, which encompasses many kinds of vectors and which is extensively studied genetically, provides good results and thus is preferred. Specific examples of host bacteria include HB101, C600, and JM109 of the EK system, and BD170, MI112, and ISW1214 of the BS system. Specific examples of vectors include pBR322 and pUC18 for the EK system, and pUB110 and pHY300PLK for the BS system.

A recombinant plasmid DNA molecule is created by cleaving a vector with a restriction enzyme followed by ligation with the above-mentioned chromosomal or PCR-amplified DNA fragment. The ligation may be achieved, for example, through the use of a DNA ligase.

Methods for transforming host bacterial strains using a recombinant DNA molecule are not particularly limited. For example, a calcium chloride method (Mandel, M. and Higa, A., *J. Mol. Biol.,* 53, 159 (1970)) may be used in the case of hosts of the EK system, and a protoplast method (Chang, C. and Cohen, S. N., *Mol. Gen. Genet.,* 168, 111 (1978)) may be used in the case of hosts of the BS system. Selection of recombinant microorganisms are performed as follows. First, microorganisms which have been transformed with DNA which contains a vector-derived DNA fragment are selected, using as an index a character which is not inactivated by insertion of exogenous chromosomal DNA fragments, such as resistance to antibiotics coded onto the vector DNA. For example, in a specific case in which pBR322 of the EK system is used as a vector, and a HindIII fragment of chromosomal DNA is inserted into the HindIII cleavage site of pBR322, the tetracycline resistant gene is inactivated, so a primary selection may be conducted by growth of the transformants that confer ampicillin resistance without having a HindIII cleavage site in the ampicillin gene. Subsequently, the selected transformants are transferred onto agar plates containing starch, using, for example, a replica method, and are then cultured so as to form colonies. By staining the starch contained in the starch-containing agar plates using an iodine-containing solution, target recombinant microorganisms can be selected as they decompose starch around the colonies.

The recombinant DNA molecule harbored by the thus-obtained recombinant microorganism can be extracted using standard procedures for preparing plasmids or phage DNAs (Maniatis, T. et al., *Molecular Cloning,* Cold Spring Harbor Laboratory, New York (1982)). When cleavage patterns obtained through the use of various restriction enzymes are analyzed by electrophoresis, it is confirmed that the recombinant DNA molecule is a ligated product of the vector DNA molecule and a DNA fragment containing the alkaline liquefying α-amylase gene.

The gene encoding an alkaline liquefying α-amylase is contained in a DNA fragment of about 2.1 kb shown in the restriction enzyme map of FIG. 1, and is present in the segment of about 1.6 kb shown by the white bar. The gene has a nucleotide sequence shown as SEQ ID NO:1. In this sequence, the 5' terminus and 3' terminus correspond to the left-hand side and the right-hand side, respectively, of the fragment of about 2.1 kb shown as SEQ ID NO:1. In this sequence is observed an open reading frame (ORF) starting at the 145th nucleotide, ATG, and coding for a sequence consisting of 516 amino acid residues described in SEQ ID NO:2. Thirteen bases (13 b) upstream of the ORF, there exists a sequence AAGGAG which is highly complementary to the 3' terminal sequence of the 16S ribosomal RNA of *Bacillus subtilis* (McLaughlin, J. R. et al., *J. Biol. Chem.,* 256, 11283 (1981)). On a further upstream region extending nucleotides from 9 to 36, there exists a sequence TTGAAA . . . 16b . . . TATGGT which has high homology with the consensus sequence of a $\sigma^A$-type promoter (Gitt, M. A. et al, *J. Biol. Chem.,* 260, 7178 (1985)). Similarly, another $\sigma^A$-type promoter sequence is found at nucleotides from 95 to 125. The amino acid sequence of the 10 amino acid residues on the amino terminus side in an alkaline liquefying α-amylase purified from a culture of Bacillus sp. KSM-AP1378 coincides with the sequence extending from the 37th amino acid (amino acid Nos. 37–46 in SEQ ID NO:2) deduced from the nucleotide sequence of the present DNA fragment.

When the nucleotide sequence of the gene of the present invention and a deduced amino acid sequence were compared with those of α-amylase known hitherto, it was confirmed that the present gene includes a novel nucleotide sequenced, with the deduced amino acid sequence encoded by the gene being different from those of other α-amylases such as a liquefying α-amylase produced by *Bacillus amylolique* (Takkinen, K. et al., *J. Biol. Chem.,* 258, 1007 (1983)), a liquefying α-amylase produced by *Bacillus stearothermophilus* (Nakajima, R. et al., *J. Bacteriol.,* 163, 401 (1985)), a liquefying α-amylase produced by *Bacillus licheniformis* (Yuuki, T et al., *J. Biol. Chem.,* 98, 1147 (1985)), or a liquefying α-amylase produced by Bacillus sp. 707 (Tsukamoto, A. et al., *Biochem. Biophys. Res. Commun.,* 151, 25 (1988)).

Figure 2:
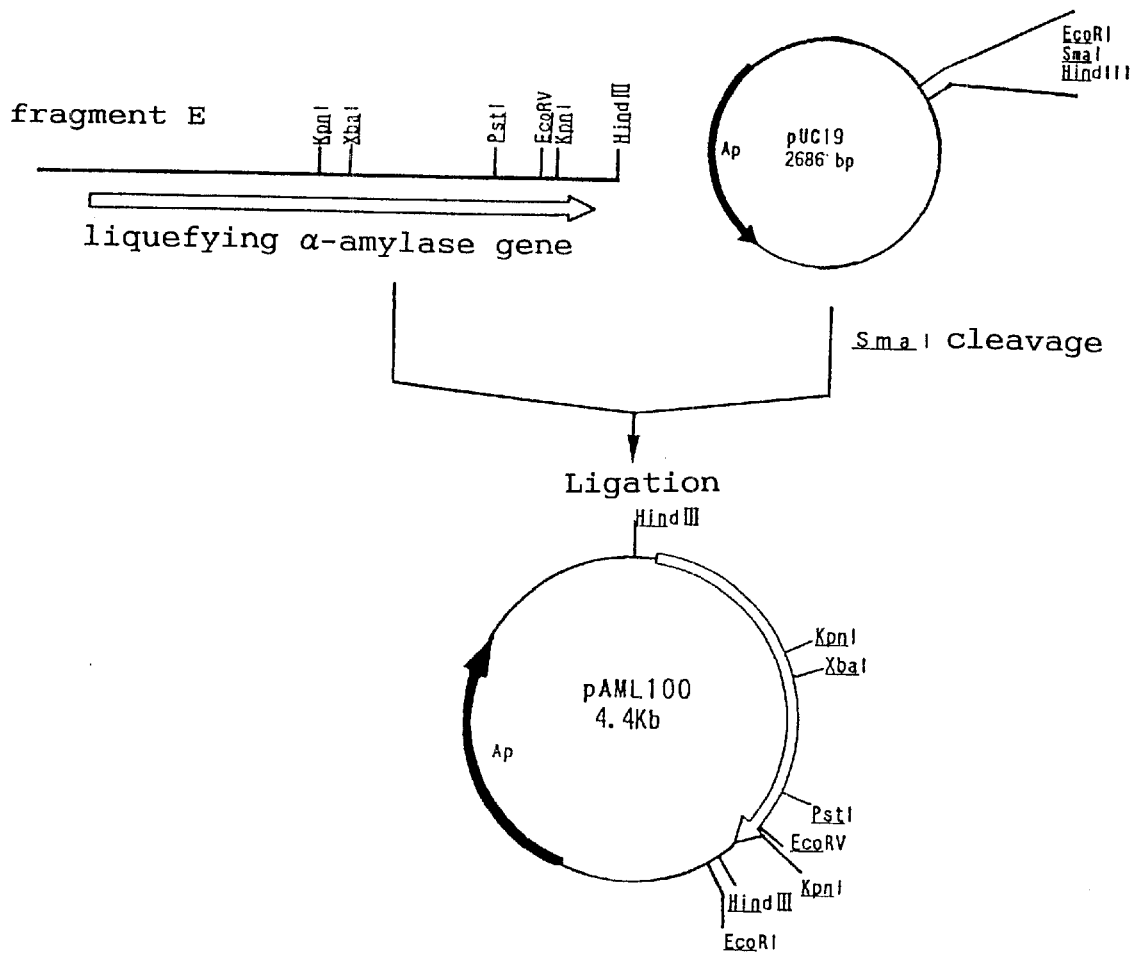
FIG. 2 is a chart depicting construction of pAML100 using a fragment of the gene encoding an alkaline liquefying amylase.
Figure 4:
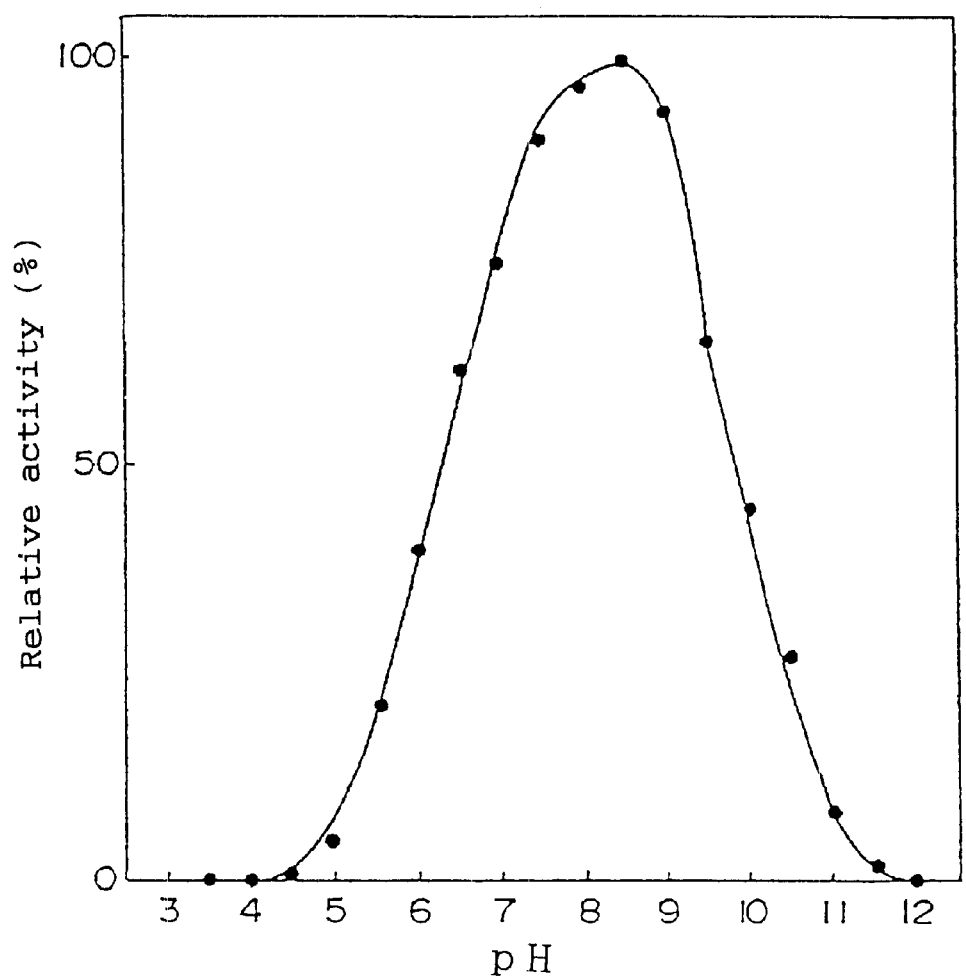
FIG. 4 is a pH profile of an alkaline liquefying α-amylase produced by Bacillus sp. KSM-AP1378.

An example of a preferred recombinant DNA molecule containing the entire region of the alkaline liquefying α-amylase gene is plasmid pAML100 (FIG. 2). This recombinant plasmid has a size of 4.4 kb and formed of a fragment containing a 1.8 kb fragment which contains the alkaline liquefying α-amylase gene and pUC19. An example of a preferred recombinant microorganism harboring the recombinant DNA molecule is an *E. coli* HB101(pAML100) strain. This strain was obtained by transforming *E. coli* HB101 strain with the recombinant plasmid pAML100 using a standard transformation method. When this strain is cultured using a medium routinely employed for culturing *E. coli*, it produces an alkaline liquefying α-amylase. The optimum reaction pH of the thus-produced enzyme is pH 8–9. This agrees well with the activity-pH relationship profile determined for the alkaline liquefying α-amylase produced by the gene donor bacterial strain, Bacillus sp. KSM-AP1378 (FIG. 4).

The DNA fragments of the present invention are not necessarily limited only to those encoding the amino acid sequences shown in the below-described sequence listing, so far as they encode a protein exhibiting the enzymatic activity of interest, and they encompass DNA fragments encoding an amino acid sequence in which one or more amino acids are substituted, added, deleted, inverted, or inserted. An example of such DNA is one encoding an amino acid sequence equivalent to the amino acid sequence described in SEQ ID NO:2 from which up to 32 amino acids on the N-terminal side have been deleted.

In order to produce an alkaline liquefying α-amylase using the transformed microorganism of the present invention, a transformed microorganism harboring the aforementioned DNA fragment of the present invention is subjected to culturing. Alternatively, the DNA fragment may be integrated in a variety of expression vectors to obtain transformed microorganisms with enhanced expression ability, followed by culturing of the resultant transformants. Moreover, the transformed microorganisms may be cultured under different conditions depending on the identity of the microorganisms. Thus, culture conditions suited for the host may be used. In order to collect an alkaline liquefying α-amylase from the resultant culture, a routine method (such as the method described in WO94/26881) may be used.

The DNA fragments of the present invention may be further used as probes for the isolation of homologous alkaline liquefying α-amylase genes from other organisms.

EXAMPLES

The present invention will next be described in more detail by way of examples, which should not be construed as limiting the invention thereto. Concentrations in the Examples are all on a basis of % by weight.

Example 1

Bacillus sp. KSM-AP1378 producing an alkaline liquefying α-amylase was inoculated in 5 ml of medium A (Table 1) and subjected to shaking culture at 30° C. for 24 hours. One ml of the culture was inoculated in 100 ml of the same medium, followed by shaking culture at 30° C. for a further 12 hours. Subsequently, cells were collected by centrifugation and about 1 mg of chromosomal DNA was obtained in accordance with a method proposed by Saito and Miura (Saito, H. and Miura K., *Biochim Biophys. Acta,* 72, 619 (1963)).

TABLE 1

| Composition of medium A | |
| --- | --- |
| Soluble starch | 1.0% |
| Polypepton | 1.0% |
| Yeast extract | 0.5% |
| $KH_2PO_4$ | 0.1% |
| $Na_2HPO_4 \cdot 12H_2O$ | 0.25% |
| $MgSO_4 \cdot 7H_2O$ | 0.02% |
| $CaCl_2 \cdot 2H_2O$ | 0.02% |
| $FeSO_4 \cdot 7H_2O$ | 0.001% |
| $MnCl_2 \cdot 4H_2O$ | 0.0001% |
| $Na_2CO_3$ | 1.0% (separately sterilized) |

Example 2

It is known that many members of the amylase family possess I–IV regions where amino acid sequences are conserved at a high level (Nakajima, R. et al., *Appl. Microbiol. Biotechnol.,* 23, 355 (1986)). Therefore, primers 1 and 2 (FIGS. 1 and 3) corresponding to regions II and IV were synthesized based on the amino acid sequence of region II and the amino acid sequence of region IV, which are particularly conserved regions among regions I through IV of known alkaline liquefying α-amylases. Using the thus-synthesized primers and chromosomal DNA of KSM-AP1378 (which served as template), PCR was conducted (one cycle=94° C.×1 min.+42° C.×1 min.+60° C.×2 min., 30 cycles). A gene fragment of approximately 0.3 kb (fragment A) shown in FIG. 1 was obtained, and the nucleotide sequence of this fragment was determined. As a result, it was found that the present fragment was coded with an amino acid sequence exhibiting a non-negligible level of homology with the amino acid sequence extending from region II through region IV of known liquefying amylase.

Example 3

Using fragment A as a probe, chromosomal DNA of XbaI-digested KSM-AP1378 was subjected to Southern hybridization. As a result, it was confirmed that there was a band which hybridized at the location of approximately 1.0 kb. An amplified fragment of approximately 0.7 kb (fragment B) was obtained by an inverse PCR method (Triglia, T. et al., *Nucleic Acids Res.*, 16, 81 (1988)) using primers synthesized from the terminal sequences of fragment A (on the side of region II: primer 3; on the side of region IV: primer 4) and DNAs which had been obtained by intramolecularly ligating XbaI-digested KSM-AP1378 chromosomal DNA (FIG. 1) as template. The nucleotide sequence of fragment B was determined, which revealed that the present fragment contained a stretch, approximately 0.6 kb region downstream from region IV. The present fragment contained a termination codon for the ORF, which was deduced to be attributed to alkaline liquefying α-amylase.

Example 4

A primer was designed and synthesized based on the N-terminal amino acid sequence (7 amino acids) of alkaline liquefying α-amylase from the KSM-AP1378 strain (FIG. 3). Using the resultant primer (primer 5) in combination with the aforementioned primer 3 (FIG. 3) and, as a template, chromosomal DNA of KSM-AP1378, PCR was conducted to obtain a fragment of approximately 0.7 kb (fragment C, FIG. 1), thereby determining its nucleotide sequence.

Example 5

A primer containing 21 bases, stretching directly downstream of the nucleotide sequence encoding N-terminal amino acid sequence of the purified enzyme, was synthesized (primer 6). Using primers 6 and 7 (FIGS. 1 and 3) and DNAs which had been obtained by intramolecularly ligating HindIII-digested KSM-AP1378 chromosomal DNA (FIG. 1) as templates, an inverse PCR method was performed, obtaining a 1.2 kb fragment in which an upstream 0.8 kb fragment (fragment D) and a downstream PstI-HindIII 0.4 kb fragment had been ligated at the HindIII site. The nucleotide sequence of the fragment D region was determined, which revealed the presence of a signal sequence composed of 31 amino acids, MKLHNRIISVLLTLLLAVAVLFPYMTEPAQA (SEQ ID NO:12)(from No. 1 to No. 31 of SEQ ID NO:1), a deduced SD sequence composed of AAGGAG (nucleotides 127–132; McLaughlin, J. R. et al., *J. Biol. Chem.*, 260, 7178 (1985)), and two kinds of deduced promoter sequences (−35 sequences, TTGAAA; −10 sequence, TATGGT, and −35 sequence, TTGACT; −10 sequence, TAAATT).

Example 6

Using primer A located at approximately 0.1 kb upstream of the promoter sequence, primer B located 79 b downstream of the termination codon, and chromosomal DNA of KSM-AP1378 as templates, a stretch of approximately 1.8 kb between the primers was amplified by PCR. The resultant amplified fragment was inserted into the SmaI site of pUC19, and then introduced into *E. Coli* HB101. The transformant was allowed to grow on an LB agar medium containing 0.4% Starch azure and 15 μg/ml ampicillin. Colonies which had formed transparent halos around them were isolated as an *E. Coli* strain that produced liquefying α-amylase. A recombinant plasmid was prepared from this transformant, and a restriction enzyme map of the plasmid was made. In the map, it was confirmed that an approximately 1.8 kb DNA fragment (fragment E) shown in FIG. 1 was contained. This recombinant plasmid was designated plasmid pAML100 (FIG. 2).

Example 7

The recombinant *E. coli* obtained in Example 6 was subjected to shaking culture for 12 hours in 5 ml of an LB liquid medium containing 50 μg/ml of ampicillin. One (1) ml of the culture was inoculated to 100 ml of an LB medium (containing ampicillin), followed by shaking culture at 37° C. for 24 hours. Cells collected by centrifugal separation were suspended in Tris-HCl buffer (pH 8.0), and were disrupted by sonication. After the cells were sonicated, cell debris was removed by centrifugal separation, and the resultant supernatant was used as a cell-free extract. As a control, the cell-free extract of HB101(PUC19) strain was separately prepared in a similar manner. α-Amylase activities in these extracts were measured by first causing a reaction, at 50° C. for 15 minutes, in a reaction mixture containing 50 mM glycine-NaCl—NaOH buffer (pH 10) and soluble starch, and then by quantitatively determining the produced reducing sugar by the 3,5-dinitrosalicylic acid method (WO94/26881). One unit of enzymatic activity was defined as the amount of protein that produced a quantity per minute of reducing sugar equivalent to 1 μmol of glucose. As a result, α-amylase activity was detected in the cell-free extract of strain HB101(pAML100). The optimum working pH of α-amylase was found to fall within the pH range between 8 and 9. This result coincides well with the optimum pH of liquefying α-amylase produced by Bacillus sp. KSM-AP1378 (FIG. 4). For the measurement of enzymatic activities, the buffers shown in Table 2 below were used (each at 40 mM).

TABLE 2

| pH 3.5–5.5: | Acetate buffer |
| pH 5.5–8.5: | Tris-maleic acid buffer |
| pH 8.5–10.5: | Glycine-NaCl-NaOH buffer |
| pH 10.5–11.0: | $Na_2CO_3$-$NaHCO_3$ buffer |

Industrial Applicability:

According to the present invention, it is possible to obtain a gene encoding for alkaline liquefying α-amylase exhibiting the maximum activity in the alkaline pH range as well as a microorganism harboring such gene. Use of them facilitates mass production of alkaline liquefying α-amylase.

SEQUENCE LISTING

<160> NUMBER OF SEQ ID NOS: 12

<210> SEQ ID NO 1
<211> LENGTH: 1776
<212> TYPE: DNA
<213> ORGANISM: Bacillus sp.
<220> FEATURE:

<221> NAME/KEY: CDS
<222> LOCATION: (145)..(1692)
<223> OTHER INFORMATION:

<400> SEQUENCE: 1

| | |
|---|---|
| atataaattt gaaatgaaca cctatgaaaa tatggtagcg attgcgcgac gagaaaaaac | 60 |
| ttgggagtta ggaagtgata ttaaaggatt tttttgact tgttgtgaaa acgcttgcat | 120 |

| | | | | | | | | | | |
|---|---|---|---|---|---|---|---|---|---|---|
| aaattgaagg agagggtgct tttt | atg<br>Met<br>1 | aaa<br>Lys | ctt<br>Leu | cat<br>His | aac<br>Asn | cgt<br>Arg | ata<br>Ile | att<br>Ile | agc<br>Ser<br>5 | 171 |
| gta<br>Val<br>10 | cta<br>Leu | tta<br>Leu | aca<br>Thr | cta<br>Leu<br>15 | ttg<br>Leu | tta<br>Leu | gct<br>Ala | gta<br>Val | gct<br>Ala<br>20 | gtt<br>Val | ttg<br>Leu | ttt<br>Phe | cca<br>Pro | tat<br>Tyr | atg<br>Met<br>25 | 219 |
| acg<br>Thr | gaa<br>Glu | cca<br>Pro | gca<br>Ala | caa<br>Gln<br>30 | gcc<br>Ala | cat<br>His | cat<br>His | aat<br>Asn | ggg<br>Gly<br>35 | acg<br>Thr | aat<br>Asn | ggg<br>Gly | acc<br>Thr | atg<br>Met<br>40 | atg<br>Met | 267 |
| cag<br>Gln | tat<br>Tyr | ttt<br>Phe | gaa<br>Glu<br>45 | tgg<br>Trp | cat<br>His | ttg<br>Leu | cca<br>Pro | aat<br>Asn<br>50 | gac<br>Asp | ggg<br>Gly | aac<br>Asn | cac<br>His | tgg<br>Trp<br>55 | aac<br>Asn | agg<br>Arg | 315 |
| tta<br>Leu | cga<br>Arg | gat<br>Asp<br>60 | gac<br>Asp | gca<br>Ala | gct<br>Ala | aac<br>Asn | tta<br>Leu<br>65 | aag<br>Lys | agt<br>Ser | aaa<br>Lys | ggg<br>Gly | att<br>Ile<br>70 | acc<br>Thr | gct<br>Ala | gtt<br>Val | 363 |
| tgg<br>Trp | att<br>Ile<br>75 | cct<br>Pro | cct<br>Pro | gca<br>Ala | tgg<br>Trp | aag<br>Lys<br>80 | ggg<br>Gly | act<br>Thr | tcg<br>Ser | caa<br>Gln | aat<br>Asn<br>85 | gat<br>Asp | gtt<br>Val | ggg<br>Gly | tat<br>Tyr | 411 |
| ggt<br>Gly<br>90 | gcc<br>Ala | tat<br>Tyr | gat<br>Asp | ttg<br>Leu | tac<br>Tyr<br>95 | gat<br>Asp | ctt<br>Leu | ggt<br>Gly | gag<br>Glu | ttt<br>Phe<br>100 | aac<br>Asn | caa<br>Gln | aag<br>Lys | gga<br>Gly | acc<br>Thr<br>105 | 459 |
| gtc<br>Val | cgt<br>Arg | aca<br>Thr | aaa<br>Lys | tat<br>Tyr<br>110 | ggc<br>Gly | aca<br>Thr | agg<br>Arg | agt<br>Ser | cag<br>Gln<br>115 | ttg<br>Leu | caa<br>Gln | ggt<br>Gly | gcc<br>Ala | gtg<br>Val<br>120 | aca<br>Thr | 507 |
| tct<br>Ser | ttg<br>Leu | aaa<br>Lys | aat<br>Asn<br>125 | aac<br>Asn | ggg<br>Gly | att<br>Ile | caa<br>Gln | gtt<br>Val<br>130 | tat<br>Tyr | ggg<br>Gly | gat<br>Asp | gtc<br>Val | gtg<br>Val<br>135 | atg<br>Met | aat<br>Asn | 555 |
| cat<br>His | aaa<br>Lys | ggt<br>Gly<br>140 | gga<br>Gly | gca<br>Ala | gac<br>Asp | ggg<br>Gly | aca<br>Thr<br>145 | gag<br>Glu | atg<br>Met | gta<br>Val | aat<br>Asn | gcg<br>Ala<br>150 | gtg<br>Val | gaa<br>Glu | gtg<br>Val | 603 |
| aac<br>Asn | cga<br>Arg | agc<br>Ser<br>155 | aac<br>Asn | cga<br>Arg | aac<br>Asn | caa<br>Gln | gaa<br>Glu<br>160 | ata<br>Ile | tca<br>Ser | ggt<br>Gly | gaa<br>Glu | tac<br>Tyr<br>165 | acc<br>Thr | att<br>Ile | gaa<br>Glu | 651 |
| gca<br>Ala | tgg<br>Trp<br>170 | acg<br>Thr | aaa<br>Lys | ttt<br>Phe | gat<br>Asp | ttc<br>Phe<br>175 | cct<br>Pro | gga<br>Gly | aga<br>Arg | gga<br>Gly | aat<br>Asn<br>180 | acc<br>Thr | cat<br>His | tcc<br>Ser | aac<br>Asn<br>185 | 699 |
| ttt<br>Phe | aaa<br>Lys | tgg<br>Trp | cgc<br>Arg<br>190 | tgg<br>Trp | tat<br>Tyr | cat<br>His | ttt<br>Phe | gat<br>Asp<br>195 | ggg<br>Gly | aca<br>Thr | gat<br>Asp | tgg<br>Trp | gat<br>Asp<br>200 | cag<br>Gln | tca<br>Ser | 747 |
| cgt<br>Arg | cag<br>Gln | ctt<br>Leu | cag<br>Gln<br>205 | aac<br>Asn | aaa<br>Lys | ata<br>Ile | tat<br>Tyr | aaa<br>Lys<br>210 | ttc<br>Phe | aga<br>Arg | ggt<br>Gly | acc<br>Thr | gga<br>Gly<br>215 | aag<br>Lys | gca<br>Ala | 795 |
| tgg<br>Trp | gac<br>Asp | tgg<br>Trp<br>220 | gaa<br>Glu | gta<br>Val | gat<br>Asp | ata<br>Ile | gag<br>Glu<br>225 | aac<br>Asn | ggc<br>Gly | aac<br>Asn | tat<br>Tyr | gac<br>Asp<br>230 | tac<br>Tyr | ctt<br>Leu | atg<br>Met | 843 |
| tat<br>Tyr | gca<br>Ala | gac<br>Asp<br>235 | att<br>Ile | gat<br>Asp | atg<br>Met | gat<br>Asp | cat<br>His<br>240 | cca<br>Pro | gaa<br>Glu | gta<br>Val | atc<br>Ile | aat<br>Asn<br>245 | gaa<br>Glu | ctt<br>Leu | aga<br>Arg | 891 |
| aat<br>Asn | tgg<br>Trp<br>250 | gga<br>Gly | gtt<br>Val | tgg<br>Trp | tat<br>Tyr | aca<br>Thr<br>255 | aat<br>Asn | aca<br>Thr | ctt<br>Leu | aat<br>Asn | cta<br>Leu<br>260 | gat<br>Asp | gga<br>Gly | ttt<br>Phe | aga<br>Arg<br>265 | 939 |
| atc<br>Ile | gat<br>Asp | gct<br>Ala | gtg<br>Val | aaa<br>Lys | cat<br>His | att<br>Ile | aaa<br>Lys | tac<br>Tyr | agc<br>Ser | tat<br>Tyr | acg<br>Thr | aga<br>Arg | gat<br>Asp | tgg<br>Trp | cta<br>Leu | 987 |

-continued

```
Ile Asp Ala Val Lys His Ile Lys Tyr Ser Tyr Thr Arg Asp Trp Leu
            270                 275                 280 aca cat gtg cgt aac acc aca ggt aaa cca atg ttt gca gtt gca gaa      1035
Thr His Val Arg Asn Thr Thr Gly Lys Pro Met Phe Ala Val Ala Glu
        285                 290                 295 ttt tgg aaa aat gac ctt gct gca atc gaa aac tat tta aat aaa aca      1083
Phe Trp Lys Asn Asp Leu Ala Ala Ile Glu Asn Tyr Leu Asn Lys Thr
    300                 305                 310 agt tgg aat cac tcc gtg ttc gat gtt cct ctt cat tat aat ttg tac      1131
Ser Trp Asn His Ser Val Phe Asp Val Pro Leu His Tyr Asn Leu Tyr
315                 320                 325 aat gca tct aat agt ggt ggc tat ttt gat atg aga aat att tta aat      1179
Asn Ala Ser Asn Ser Gly Gly Tyr Phe Asp Met Arg Asn Ile Leu Asn
330                 335                 340                 345 ggt tct gtc gta caa aaa cac cct ata cat gca gtc aca ttt gtt gat      1227
Gly Ser Val Val Gln Lys His Pro Ile His Ala Val Thr Phe Val Asp
                350                 355                 360 aac cat gac tct cag cca gga gaa gca ttg gaa tcc ttt gtt caa tcg      1275
Asn His Asp Ser Gln Pro Gly Glu Ala Leu Glu Ser Phe Val Gln Ser
            365                 370                 375 tgg ttc aaa cca ctg gca tat gca ttg att ctg aca agg gag caa ggt      1323
Trp Phe Lys Pro Leu Ala Tyr Ala Leu Ile Leu Thr Arg Glu Gln Gly
        380                 385                 390 tac cct tcc gta ttt tac ggt gat tac tac ggt ata cca act cat ggt      1371
Tyr Pro Ser Val Phe Tyr Gly Asp Tyr Tyr Gly Ile Pro Thr His Gly
    395                 400                 405 gtt cct tcg atg aaa tct aaa att gat cca ctt ctg cag gca cgt caa      1419
Val Pro Ser Met Lys Ser Lys Ile Asp Pro Leu Leu Gln Ala Arg Gln
410                 415                 420                 425 acg tat gcc tac gga acc caa cat gat tat ttt gat cat cat gat att      1467
Thr Tyr Ala Tyr Gly Thr Gln His Asp Tyr Phe Asp His His Asp Ile
                430                 435                 440 atc ggc tgg acg aga gaa ggg gac agc tcc cac cca aat tca gga ctt      1515
Ile Gly Trp Thr Arg Glu Gly Asp Ser Ser His Pro Asn Ser Gly Leu
            445                 450                 455 gca act att atg tcc gat ggg cca ggg ggt aat aaa tgg atg tat gtc      1563
Ala Thr Ile Met Ser Asp Gly Pro Gly Gly Asn Lys Trp Met Tyr Val
        460                 465                 470 ggg aaa cat aaa gct ggc caa gta tgg aga gat atc acc gga aat agg      1611
Gly Lys His Lys Ala Gly Gln Val Trp Arg Asp Ile Thr Gly Asn Arg
    475                 480                 485 tct ggt acc gtc acc att aat gca gat ggt tgg ggg aat ttc act gta      1659
Ser Gly Thr Val Thr Ile Asn Ala Asp Gly Trp Gly Asn Phe Thr Val
490                 495                 500                 505 aac gga ggg gca gtt tcg gtt tgg gtg aag caa taaataagga acaagaggcg    1712
Asn Gly Gly Ala Val Ser Val Trp Val Lys Gln
                510                 515 aaaattactt tcctacatgc agagctttcc gatcactcat acacccaata taaattggaa    1772
gctt                                                                1776

<210> SEQ ID NO 2
<211> LENGTH: 516
<212> TYPE: PRT
<213> ORGANISM: Bacillus sp.

<400> SEQUENCE: 2

Met Lys Leu His Asn Arg Ile Ile Ser Val Leu Leu Thr Leu Leu
1               5                   10                  15

Ala Val Ala Val Leu Phe Pro Tyr Met Thr Glu Pro Ala Gln Ala His
```

```
                     20                  25                  30
        His Asn Gly Thr Asn Gly Thr Met Met Gln Tyr Phe Glu Trp His Leu
                     35                  40                  45

Pro Asn Asp Gly Asn His Trp Asn Arg Leu Arg Asp Asp Ala Ala Asn
         50                  55                  60

Leu Lys Ser Lys Gly Ile Thr Ala Val Trp Ile Pro Ala Trp Lys
        65                   70                  75                  80

Gly Thr Ser Gln Asn Asp Val Gly Tyr Gly Ala Tyr Asp Leu Tyr Asp
                         85                  90                  95

Leu Gly Glu Phe Asn Gln Lys Gly Thr Val Arg Thr Lys Tyr Gly Thr
                        100                 105                 110

Arg Ser Gln Leu Gln Gly Ala Val Thr Ser Leu Lys Asn Asn Gly Ile
                        115                 120                 125

Gln Val Tyr Gly Asp Val Val Met Asn His Lys Gly Gly Ala Asp Gly
                        130                 135                 140

Thr Glu Met Val Asn Ala Val Glu Val Asn Arg Ser Asn Arg Asn Gln
        145                 150                 155                 160

Glu Ile Ser Gly Glu Tyr Thr Ile Glu Ala Trp Thr Lys Phe Asp Phe
                        165                 170                 175

Pro Gly Arg Gly Asn Thr His Ser Asn Phe Lys Trp Arg Trp Tyr His
                        180                 185                 190

Phe Asp Gly Thr Asp Trp Asp Gln Ser Arg Gln Leu Gln Asn Lys Ile
                        195                 200                 205

Tyr Lys Phe Arg Gly Thr Gly Lys Ala Trp Asp Trp Glu Val Asp Ile
                        210                 215                 220

Glu Asn Gly Asn Tyr Asp Tyr Leu Met Tyr Ala Asp Ile Asp Met Asp
        225                 230                 235                 240

His Pro Glu Val Ile Asn Glu Leu Arg Asn Trp Gly Val Trp Tyr Thr
                        245                 250                 255

Asn Thr Leu Asn Leu Asp Gly Phe Arg Ile Asp Ala Val Lys His Ile
                        260                 265                 270

Lys Tyr Ser Tyr Thr Arg Asp Trp Leu Thr His Val Arg Asn Thr Thr
                        275                 280                 285

Gly Lys Pro Met Phe Ala Val Ala Glu Phe Trp Lys Asn Asp Leu Ala
                        290                 295                 300

Ala Ile Glu Asn Tyr Leu Asn Lys Thr Ser Trp Asn His Ser Val Phe
        305                 310                 315                 320

Asp Val Pro Leu His Tyr Asn Leu Tyr Asn Ala Ser Asn Ser Gly Gly
                        325                 330                 335

Tyr Phe Asp Met Arg Asn Ile Leu Asn Gly Ser Val Val Gln Lys His
                        340                 345                 350

Pro Ile His Ala Val Thr Phe Val Asp Asn His Asp Ser Gln Pro Gly
                        355                 360                 365

Glu Ala Leu Glu Ser Phe Val Gln Ser Trp Phe Lys Pro Leu Ala Tyr
                        370                 375                 380

Ala Leu Ile Leu Thr Arg Glu Gln Gly Tyr Pro Ser Val Phe Tyr Gly
        385                 390                 395                 400

Asp Tyr Tyr Gly Ile Pro Thr His Gly Val Pro Ser Met Lys Ser Lys
                        405                 410                 415

Ile Asp Pro Leu Leu Gln Ala Arg Gln Thr Tyr Ala Tyr Gly Thr Gln
                        420                 425                 430

His Asp Tyr Phe Asp His His Asp Ile Ile Gly Trp Thr Arg Glu Gly
                        435                 440                 445
```

```
Asp Ser Ser His Pro Asn Ser Gly Leu Ala Thr Ile Met Ser Asp Gly
    450                 455                 460

Pro Gly Gly Asn Lys Trp Met Tyr Val Gly Lys His Lys Ala Gly Gln
465                 470                 475                 480

Val Trp Arg Asp Ile Thr Gly Asn Arg Ser Gly Thr Val Thr Ile Asn
            485                 490                 495

Ala Asp Gly Trp Gly Asn Phe Thr Val Asn Gly Gly Ala Val Ser Val
            500                 505                 510

Trp Val Lys Gln
        515

<210> SEQ ID NO 3
<211> LENGTH: 22
<212> TYPE: DNA
<213> ORGANISM: Artificial Sequence
<220> FEATURE:
<223> OTHER INFORMATION: Primer 1 corresponding to sequences on the
      upstream side of the 5'-terminus and on the downstream side of
      the 3'-terminus of the essential region based on the Bacillus sp..
<221> NAME/KEY: misc_feature
<222> LOCATION: (1)..(22)
<223> OTHER INFORMATION: n = a, c, t, g, any, unknown, or other

<400> SEQUENCE: 3
tngaygcngt naarcayath aa                                      22

<210> SEQ ID NO 4
<211> LENGTH: 26
<212> TYPE: DNA
<213> ORGANISM: Artificial Sequence
<220> FEATURE:
<223> OTHER INFORMATION: Primer 2 corresponding to sequences on the
      upstream side of the 5'-terminus and on the downstream side of
      the 3'-terminus of the essential region based on the Bacillus sp..
<221> NAME/KEY: misc_feature
<222> LOCATION: (1)..(26)
<223> OTHER INFORMATION: n = a, c, t, g, any, unknown, or other

<400> SEQUENCE: 4
tcrtgrttrt cnacraangt nacngc                                  26

<210> SEQ ID NO 5
<211> LENGTH: 23
<212> TYPE: DNA
<213> ORGANISM: Artificial Sequence
<220> FEATURE:
<223> OTHER INFORMATION: Primer 3 corresponding to sequences on the
      upstream side of the 5'-terminus and on the downstream side of
      the 3'-terminus of the essential region based on the Bacillus sp..

<400> SEQUENCE: 5
agccaatctc tcgtatagct gta                                     23

<210> SEQ ID NO 6
<211> LENGTH: 22
<212> TYPE: DNA
<213> ORGANISM: Artificial Sequence
<220> FEATURE:
<223> OTHER INFORMATION: Primer 4 corresponding to sequences on the
      upstream side of the 5'-terminus and on the downstream side of
      the 3'-terminus of the essential region based on the Bacillus sp..

<400> SEQUENCE: 6
gtacaaaaac accctataca tg                                      22
```

<210> SEQ ID NO 7
<211> LENGTH: 20
<212> TYPE: DNA
<213> ORGANISM: Artificial Sequence
<220> FEATURE:
<223> OTHER INFORMATION: Primer 5 corresponding to sequences on the
      upstream side of the 5'-terminus and on the downstream side of
      the 3'-terminus of the essential region based on the Bacillus sp..

<400> SEQUENCE: 7
aatggwacwa tgatgcakta                                              20

<210> SEQ ID NO 8
<211> LENGTH: 22
<212> TYPE: DNA
<213> ORGANISM: Artificial Sequence
<220> FEATURE:
<223> OTHER INFORMATION: Primer 6 corresponding to sequences on the
      upstream side of the 5'-terminus and on the downstream side of
      the 3'-terminus of the essential region based on the Bacillus sp..

<400> SEQUENCE: 8
catttggcaa atgccattca aa                                           22

<210> SEQ ID NO 9
<211> LENGTH: 21
<212> TYPE: DNA
<213> ORGANISM: Artificial Sequence
<220> FEATURE:
<223> OTHER INFORMATION: Primer 7 corresponding to sequences on the
      upstream side of the 5'-terminus and on the downstream side of
      the 3'-terminus of the essential region based on the Bacillus sp..

<400> SEQUENCE: 9
aaaattgatc cacttctgca g                                            21

<210> SEQ ID NO 10
<211> LENGTH: 26
<212> TYPE: DNA
<213> ORGANISM: Artificial Sequence
<220> FEATURE:
<223> OTHER INFORMATION: Primer A corresponding to sequences on the
      upstream side of the 5'-terminus and on the downstream side of
      the 3'-terminus of the essential region based on the Bacillus sp..

<400> SEQUENCE: 10
cagcgcgtga taatataaat ttgaat                                       26

<210> SEQ ID NO 11
<211> LENGTH: 26
<212> TYPE: DNA
<213> ORGANISM: Artificial Sequence
<220> FEATURE:
<223> OTHER INFORMATION: Primer B corresponding to sequences on the
      upstream side of the 5'-terminus and on the downstream side of
      the 3'-terminus of the essential region based on the Bacillus sp..

<400> SEQUENCE: 11
aagcttccaa tttatattgg gtgtat                                       26

<210> SEQ ID NO 12
<211> LENGTH: 31
<212> TYPE: PRT
<213> ORGANISM: Bacillus sp.

<400> SEQUENCE: 12

Met Lys Leu His Asn Arg Ile Ile Ser Val Leu Leu Thr Leu Leu Leu
1               5                   10                  15

-continued

```
Ala Val Ala Val Leu Phe Pro Tyr Met Thr Glu Pro Ala Gln Ala
            20                  25                  30
```

What is claimed is:

1. An isolated DNA molecule, which encodes the amino acid sequence described in SEQ ID NO:2 or a fragment thereof having α-amylase activity.

2. A recombinant DNA containing the DNA molecule of claim 1.

3. A transformed microorganism harboring the recombinant DNA of claim 2.

4. A method for producing alkaline liquefying α-amylase, comprising culturing the transformed microorganism of claim 3 and isolating the alkaline liquefying α-amylase produced by the microorganism.

5. The recombinant DNA plasmid pAML100.

6. The recombinant *E. coli* strain HB101 (pAML100).

* * * * *